(12) United States Patent
Oka et al.

(10) Patent No.: US 6,417,327 B1
(45) Date of Patent: Jul. 9, 2002

US006417327B1

(54) PEPTIDE CAPABLE OF REGULATING PHYSIOLOGICAL FUNCTION OF FGF-5 AND PHARMACEUTICAL COMPOSITION CONTAINING THE PEPTIDE

(75) Inventors: Shuichi Oka; Yoshimitsu Yamazaki, both of Ibaraki; Toru Imamura, Tokyo; Yasuko Fujita, Ibaraki; Saori Yamamoto, Ibaraki; Yukiko Okita, Ibaraki; Kazuo Ozawa, Chiba; Reiko Akakura, Chiba; Chikako Ito, Ibaraki, all of (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/537,817

(22) Filed: Mar. 22, 2000

(30) Foreign Application Priority Data

Mar. 30, 1999 (JP) ............................................ 11-088364
Jan. 14, 2000 (JP) ........................................ 2000-006643

(51) Int. Cl.⁷ .............................................. C07K 14/50
(52) U.S. Cl. ...................... 530/326; 530/300; 530/327; 530/329; 530/330
(58) Field of Search ................................ 530/300, 326, 530/327, 329, 330; 514/14, 13

(56) References Cited
PUBLICATIONS

Zhan et al., Mol. Cell Biol. 8(8):3487–3495, Aug. 1988.*
Hattori et al, Biochim. Biophys. Acta 1306:31–33, 1996.*
Ozawa et al. J. Biol. Chem. 273(44):29262–71, Oct. 1998.*
Mayo, K.H., Trends in Biotechnology, 18:212–217, May, 2000/.*
Ranney, D.F., Biochemical Pharmacology, 59:105–114, 1999.*
Das, et al., Proc. Natl. Acad. Sci. USA, 90:3058–3062, Apr., 1993.*
Archimbaud et al., Leukemia Research 22:1155–1164, 1998.*

* cited by examiner

Primary Examiner—Phillip Gambel
(74) Attorney, Agent, or Firm—Fish & Richardson P.C.

(57) ABSTRACT

The present invention provides a peptide partially comprising an amino acid sequence of FGF-5 or FGF-5S (i.e., the alternatively spliced form of FGF-5), the peptide being capable of controlling physiological function(s) of FGF-5. A pharmaceutical composition containing the peptide of the invention as an active component may regulate the physiological function(s) of FGF-5 such as regulation of development or growth of a head or body hair, regulation of nutrition or function of a cranial nerve system, regulation of platelets, and/or promotion or inhibition of proliferation or differentiation of a vascular endothelial cell.

5 Claims, 5 Drawing Sheets

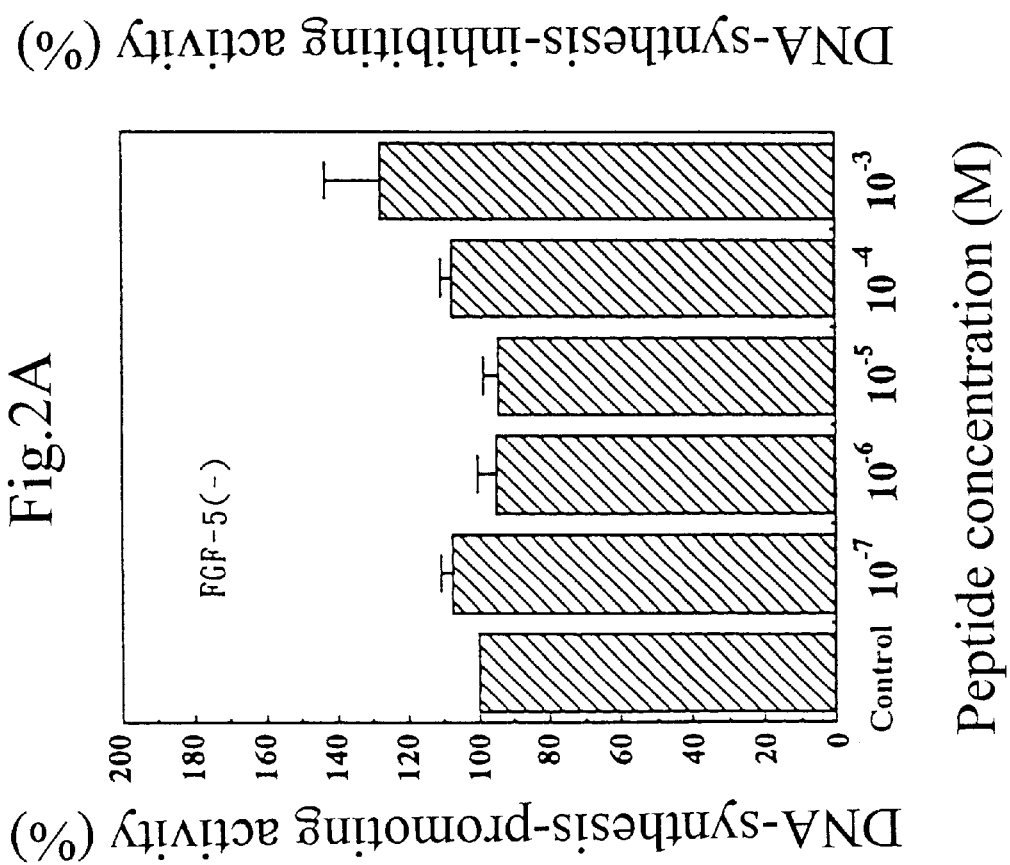

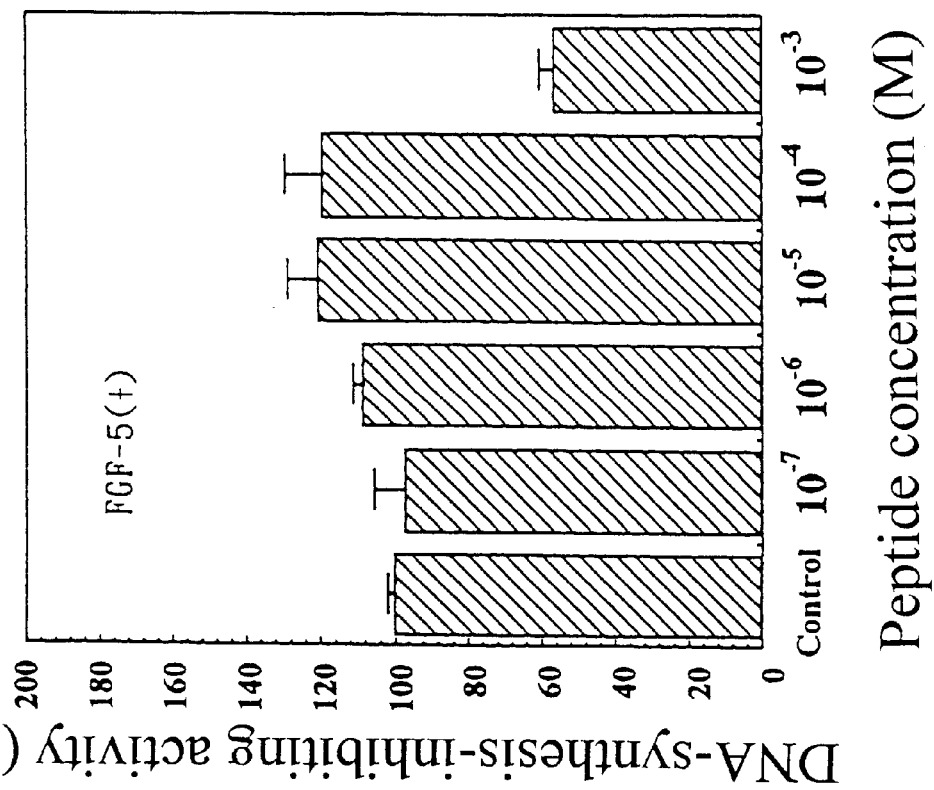
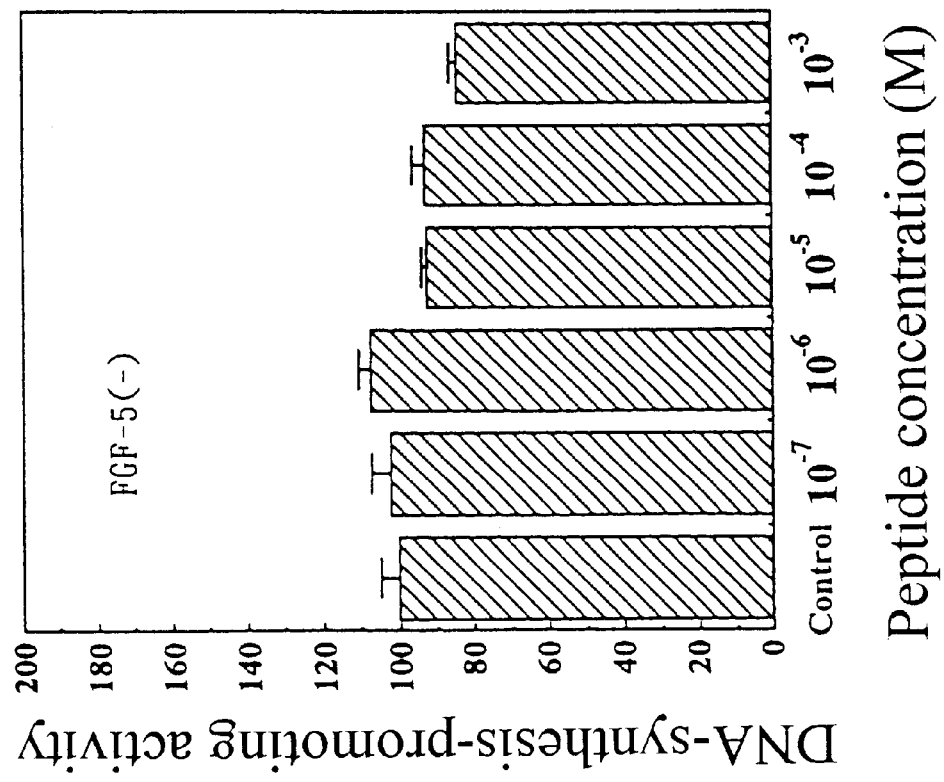

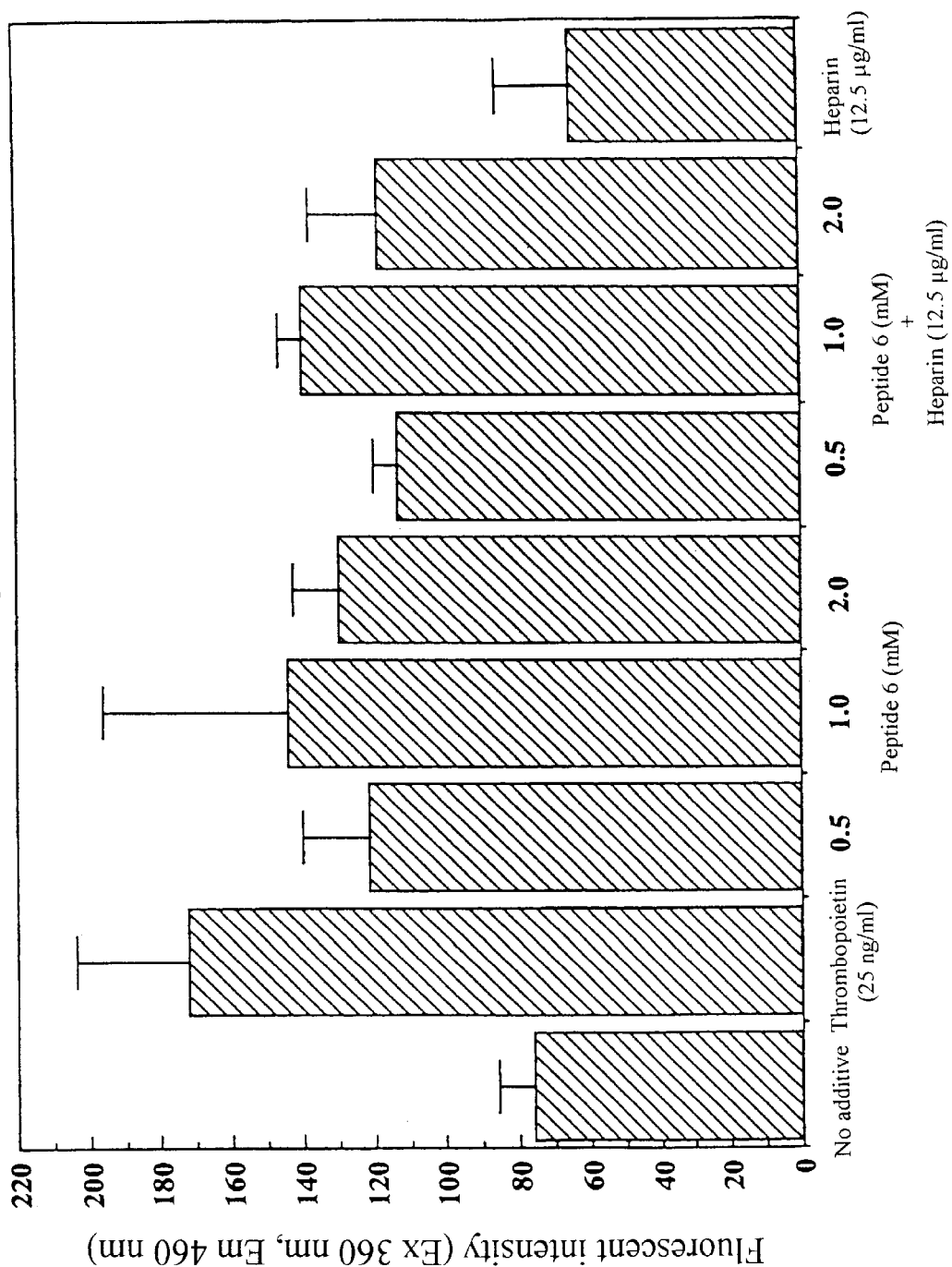

US 6,417,327 B1

PEPTIDE CAPABLE OF REGULATING PHYSIOLOGICAL FUNCTION OF FGF-5 AND PHARMACEUTICAL COMPOSITION CONTAINING THE PEPTIDE

FIELD OF THE INVENTION

The present invention relates to peptides capable of regulating various physiological functions of Fibroblast Growth Factor-5 (hereinafter, referred to as "FGF-5"), and to a pharmaceutical composition containing the peptide as an active component.

BACKGROUND OF THE INVENTION

FGF-5 is a secretory protein whose expression can be observed in a central nervous system. FGF-5 is known to have physiological functions such as fibroblast proliferation promoting activity and fibroblast mutating activity. FGF-5 is also known to change the proliferation ability of an NIH3T3 fibroblast cell transformed by introducing FGF-5 gene under the control of a permanent expression promoter. The transformed cell secretes FGF-5 into a culture supernatant, which strikingly promotes proliferation of Balb/c3T3 (one of other kinds of fibroblast) and a vascular endothelial cell. FGF-5 polypeptide expressed by introducing an FGF-5 gene expression plasmid into $E.coli$ also remarkably promotes the proliferation of Balb/c3T3 and a vascular endothelial cell.

FGF-5 is also known for its activity as a neurotrophic factor for supporting the survival of neurocyte. FGF-5 is also expressed in skeletal muscle cells. Both of FGF-5 contained in a skeletal muscle cell extract and FGF-5 expressed by introducing FGF-5 gene expression plasmid in E.coli are known to remarkably promote the survival of cultured motoneurons. This fact strongly suggests that FGF-5 is a neurotrophic factor for motoneurons. FGF-5 is also known to be expressed in mouse and rat brains. From an experiment of a primary culture of a cranial nerve cell, FGF-5 is considered to behave as a neurotrophic factor for cholinergic and serotonergic neurocytes in brain.

Analysis of recently-developed FGF-5 knockout mouse suggests that FGF-5 is involved in a hair growth cycle. Most components effective for promoting or inhibiting the development or growth of a head or body hair are conventionally obtained as synthetic compounds or by screening natural substances derived from plants or microorganisms for those having the activity by using model animals. However, since nutritional environment of the hair root has been the prior consideration in developing hair development promoting or inhibiting agent or a hair growth agent which contains the above-mentioned active component, most studies focused on anti-inflammation or disinfection of the skin, inhibition of androgen, and improvement or inhibition of the blood circulation of the treated point or the environmental conditions of the hair root. Thus, no attention has been paid so far to the principle of the mechanism of an animal hair generation, and accordingly there may be a chance that FGF-5 involved in the control of the hair growth cycle may be used to obtain a hair development or hair growth regulating agent based on the mechanism of an animal hair generation.

FGF-5 protein is known to have a structure of serially linked Exons 1, 2 and 3, which is obtained by transcribing an FGF-5-protein-coding gene to mRNA and splicing the transcript to form mature mRNA comprising serially linked Exons 1, 2 and 3. The translation frame starts from the translation starting codon ATG (which encodes methionine) in Exon 1, across Exon 2 to the stop codon in Exon 3, and produces a protein having 268 amino acids (in the case of human) or a protein having 264 amino acids (in the case of mouse) [Zhan X. et al., *Mol. Cell. Biol.*, Vol. 8, pp. 3487–3495 (1988); Haub, O. et al., *Proc. Natl. Acad., Sci., USA*, Vol. 87, pp. 8022–8026 (1990)]. Furthermore, FGF-5S, an alternatively spliced form of FGF-5 lacking Exon 2 was found, which was selectively expressed in brain and skin of human and mouse and the structure thereof have been determined [Ozawa, K. et al., *J. Biol. Chem.*, Vol.273 (44), pp.29262–29271 (1998) and Japanese Patent Application Laid-Open No. 8-75994]. FGF-5S by itself exerted a weak activity as a neurotrophic factor while it also exhibited an activity as an antagonist of FGF-5 [Ozawa, K. et al, *J. Biol. Chem.*, Vol. 273 (44), pp. 29261–29271 (1998)].

Since FGF-5 has various functions such as promoting cellular proliferation, supporting survival and differentiation of neurocytes and controlling hair growth cycle, there has been a demand for finding and studying a substance for controlling the physiological functions of FGF-5.

Platelets play an important role in the hemostatis of organisms, and formation of thrombus. Accordingly, there has been a demand for a substance for increasing the number of platelets, which may be used as a drug for regulating the platelets to counter thrombocytopenia resulting from the side-effects of chemotherapy of cancer or from serious infectious disease. Platelets and parents of platelets (i.e., megakaryocytes) are formed through differentiation, proliferation and maturation of a pluripotent blood stem cell via the action of a hematopoietic factor. Thrombopoietin has recently been reported as the hematopoietic factor involved in the differentiation to give megakaryocytes. However, since administration of thrombopoietin has also been reported to induce antibody production, thrombopoietin is presently considered not suitable as a platelet increasing substance. Accordingly, there has also been a demand for finding and studying a low-molecular controlling substance that has a differentiating activity to give the megakaryocyte without any side-effect.

The present inventors have gone through intensive study to solve the above-described problems, regarding amino acid sequences of FGF-5 and FGF-5S (i.e., the alternatively spliced form of FGF-5), and found that a peptide fragment (hereinafter, referred to as a "FGF-5 peptide") partially containing one of these amino acid sequences had an ability of controlling physiological functions of FGF-5, thereby accomplishing the present invention.

SUMMARY OF THE INVENTION

Thus, the present invention provides either: (a) a peptide comprising the entire amino acid sequence shown in SEQ ID NO: 1, or a continuous part of the amino acid sequence shown in SEQ ID NO: 1; or (b) a peptide comprising the amino acid sequence shown in SEQ ID NO: 1 optionally added with 1 to 10 amino acids at the both ends, and having an activity of controlling a physiological function of FGF-5.

Furthermore, the present invention provides either: (a) a peptide comprising the entire amino acid sequence shown in SEQ ID NO: 2, or a continuous part of the amino acid sequence shown in SEQ ID NO: 2; or (b) a peptide comprising the amino acid sequence shown in SEQ ID NO: 2 optionally added with 1 to 10 amino acids at the both ends, and having an activity of controlling a physiological function of FGF-5.

The present invention also provides a peptide of any one of: (a) a peptide comprising the amino acid sequence shown in SEQ ID NO: 3; (b) a peptide comprising an amino acid sequence having one amino acid substitution in the amino acid sequence shown in SEQ ID NO: 3, and having an activity of controlling a physiological function of FGF-5; or (c) a peptide comprising the amino acid sequence shown in SEQ ID NO: 3 optionally added with 1 to 10 amino acids at the N-terminus thereof, and having an activity of controlling a physiological function of FGF-5.

The present invention also provides a peptide of any one of: (a) a peptide comprising the amino acid sequence shown in SEQ ID NO: 4; (b) a peptide comprising an amino acid sequence having one amino acid substitution in the amino acid sequence shown in SEQ ID NO: 4, and having an activity of controlling a -physiological function of FGF-5; or (c) a peptide comprising the amino acid sequence shown in SEQ ID NO: 4 optionally added with 1 to 10 amino acids at the N-terminus thereof, and having an activity of controlling a physiological function of FGF-5.

Examples of the physiological function of FGF-5 include regulating hair development or hair growth, regulating nutrition or function of cranial nerve system, regulating platelets, and promoting or inhibiting proliferation or differentiation of a vascular endothelial cell, a fibroblast, a myoblast, a chondrocyte, an osteoblast or a glia cell.

The present invention further provides a pharmaceutical composition comprising any one of the above-described peptides.

This specification includes all or part of the contents as disclosed in the specifications of Japanese Patent Application Nos. 11-88364 and 2000-6643, which are priority documents of the present application.

BRIEF DESCRIPTION OF THE DRAWINGS

FIGS. 2A and 2B are bar charts showing the results of DNA-synthesis-promoting activity, and DNA-synthesis-inhibiting activity of FGF-5 peptide 3, respectively;

FIGS. 3A and 3B are bar charts showing the results of DNA-synthesis-promoting activity, and DNA-synthesis-inhibiting activity of FGF-5 peptide 4, respectively;

FIG. 5 is a bar chart showing the results of the proliferating and differentiating activities of FGF-5 peptide 6 to give megakaryocytes.

DETAILED DESCRIPTION OF THE INVENTION

Figure 1B:
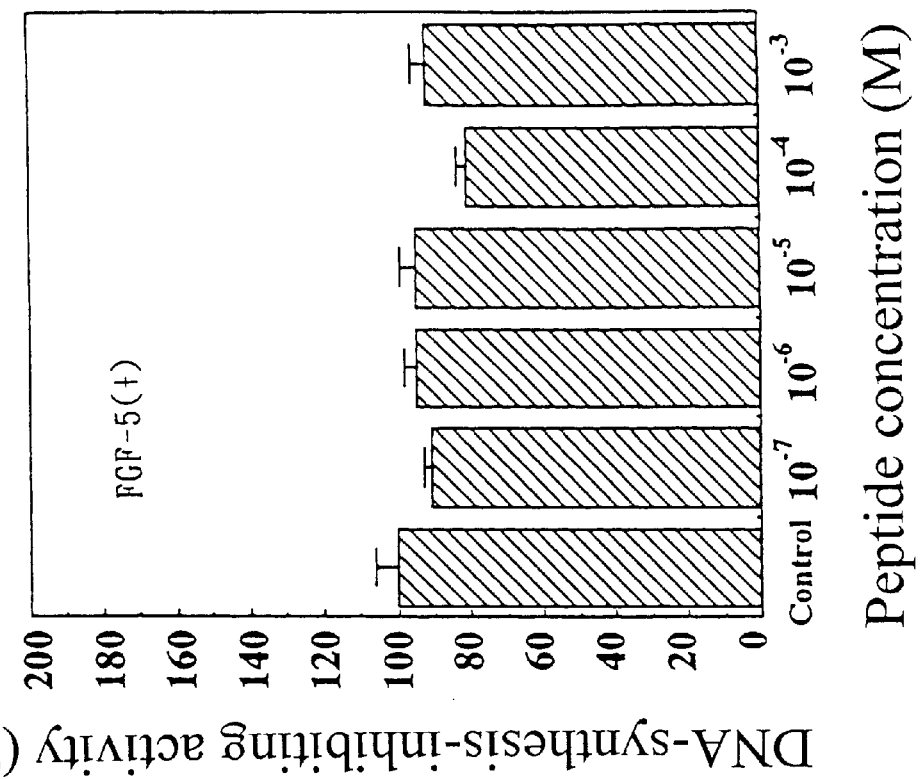
FIGS. 1A and 1B are bar charts showing the results of DNA-synthesis-promoting activity, and DNA-synthesis-inhibiting activity of FGF-5 peptide 1, respectively.

A peptide of the present invention (hereinafter, referred to as a "FGF-5 peptide") having an activity of controlling physiological functions of FGF-5 is present in an amino acid sequence of FGF-5 protein or in an amino acid sequence of FGF-5S protein. The FGF-5 peptide controls the physiological functions of FGF-5 by exerting an activity of promoting the physiological functions of FGF-5 (as an FGF-5 agonist) or an activity of inhibiting the physiological functions of FGF-5 (as an FGF-5 antagonist).

A first peptide having a promoting effect on the physiological functions of FGF-5 is either: (a) a peptide comprising the entire amino acid sequence shown in SEQ ID NO: 1, or a continuous part of the amino acid sequence shown in SEQ ID NO: 1; or (b) a peptide comprising the amino acid sequence shown in SEQ ID NO: 1 optionally added with 1 to 10 amino acids at the both ends, and having an activity of controlling a physiological function of FGF-5.

Examples of the continuous part of the amino acid sequence of SEQ ID NO: 1 include amino acid sequences represented by SEQ ID NOS: 5, 6 and 9.

A second peptide having a promoting effect on the physiological functions of FGF-5 is either: (a) a peptide comprising the entire amino acid sequence shown in SEQ ID NO: 2, or a continuous part of the amino acid sequence shown in SEQ ID NO: 2; or (b) a peptide comprising the amino acid sequence shown in SEQ ID NO: 2 optionally added with 1 to 10 amino acids at the both ends, and having an activity of controlling a physiological function of FGF-5.

Examples of the continuous part of the amino acid sequence of SEQ ID NO: 2 include amino acid sequences represented by SEQ ID NOS: 5 and 7.

On the other hand, a first peptide having an inhibiting effect on the physiological functions of FGF-5 is any one of: (a) a peptide comprising the amino acid sequence shown in SEQ ID NO: 3; (b) a peptide comprising an amino acid sequence having one amino acid substitution in the amino acid sequence shown in SEQ ID NO: 3, and having an activity of controlling a physiological function of FGF-5; or (c) a peptide comprising the amino acid sequence shown in SEQ ID NO: 3 optionally added with 1 to 10 amino acids at the N-terminus thereof, and having an activity of controlling a physiological function of FGF-5.

The above-mentioned amino acid substitution includes substitution of Val by Leu or Ala in the amino acid sequence shown in SEQ ID NO: 3.

The amino acid sequence having 1 to 10 optional amino acids added to the N-terminus thereof includes, for example, the amino acid sequence shown in SEQ ID NO: 8.

A second peptide having an inhibiting effect on the physiological functions of FGF-5 is any one of: (a) a peptide comprising the amino acid sequence shown in SEQ ID NO: 4; (b) a peptide comprising an amino acid sequence having one amino acid substitution in the amino acid sequence shown in SEQ ID NO: 4, and having an activity of controlling a physiological function of FGF-5; or (c) a peptide comprising the amino acid sequence shown in SEQ ID NO: 4 optionally added with 1 to 10 amino acids at the N-terminus thereof, and having an activity of controlling a physiological function of FGF-5.

The above-mentioned amino acid substitution includes substitution of Ile by Val or Leu in the amino acid sequence shown in SEQ ID NO: 4.

Each of the above-mentioned peptides may be obtained by organic chemical synthesis, or by hydrolyzing a protein using any method such as an enzymatic method.

Examples of the physiological functions of FGF-5 that can be controlled by the FGF-5 peptide of the invention include regulation of development or growth of a head or body hair, regulation of nutrition or function of a cranial nerve system, regulation of platelets, and promotion or inhibition of proliferation or differentiation of a vascular endothelial cell, a fibroblast, a myoblast, a chondrocyte, an osteoblast or a glia cell.

Accordingly, the FGF-5 peptide of the invention is useful as an FGF-5 antagonist for promoting hair development, and preventing and treating various diseases such as fibroblastoma, angioma, osteoblastoma and neuroblastoma. The FGF-5 peptide of the invention is also useful as an FGF-5 agonist for regulating hair development (as by FGF-5), preventing and treating various diseases such as neurocyte death, Alzheimer's disease, Parkinson's disease, amnesia, dementia, cardiac infarction, thrombopenic purpura and thrombocytopenia caused by chemotherapy of cancer or by serious infective disease.

The FGF-5 peptide of the invention may be formulated into a pharmaceutical composition in the form of solution, lotion, aerosol, injection, powder, granule, tablet, suppository, enteric coated tablet, capsule or the like, for example, by a known method using a pharmaceutically acceptable solvent, vehicle, carrier, adjuvant or the like. The content of the FGF-5 peptide as an active component in the pharmaceutical composition may be about 0.0000000001 to 1.0 percent by weight.

The pharmaceutical composition may be used as an agent for preventing or treating various diseases such as those mentioned above, or as a reagent used for a research. Specifically, the pharmaceutical composition may be administered orally or parenterally, for example, to a mammal such as human, mouse, rat, rabbit, dog or cat, as a hair developing agent, a hair growing agent, a nutrient or function controlling agent for a cranial nerve system, an agent for enhancing learning ability or a platelet regulating agent. The dose of the pharmaceutical composition of the invention may suitably be determined depending on the form of the composition, administration route and symptom. For example, in the case of a mammal (including human), 0.0001–1000 mg of FGF-5 peptide of the invention may be administered for several times a day.

EXAMPLES

Hereinafter, the present invention will be described by way of examples which do not limit the scope of the invention.

Reference Example 1

Preparation of Recombinant FGF-5 Protein

Recombinant FGF-5 was obtained according to the description of Ozawa K. et al., *J. Biol. Chem.*, Vol.273 (44), pp. 29262–29271 (1998).

Specifically, RNA was extracted from a 6-week-old ICR mouse brain. From the mouse RNA, a cDNA mixture was obtained by using M-HLV reverse transcriptase and random hexanucleotide DNA as a primer. The gene of interest was amplified from the cDNA mixture by PCR reaction. As a result, a DNA fragment with a size corresponding to the size of FGF-5 protein was obtained, which was then separated by gel electrophoresis and excised from the gel. The DNA fragment was inserted into the cloning site of cloning vector pET-3 to construct a plasmid. Using the plasmid as a vector and *E. coli* strain BL21 (DE3) pLysS as a host, a transformant was obtained.

The transformant was plated and cultured on 40 ml LB medium at 37° C. for 16 hours, and further cultured in a fresh medium. One mM isopropyl thiogalactoside (IPTG) was added as an inducer and the transformant was further cultured for 3 hours. The resultant culture was centrifuged at 6,000 rpm for 15 min. to obtain the cells. The cells were placed in a test tube to be disrupted by intermittent ultrasonication in an ice bath for 2 min., and centrifuged at 12,000 rpm for 1 hour. The supernatant containing the recombinant FGF-5 protein was collected.

The recombinant FGF-5 protein was purified as follows. First, heparin-sepharose was suspended and washed in 10 mM Tris/HCl buffer (pH 7.4). The ultrasonicated and centrifuged supernatant sample obtained above was added to a buffer containing NaCl (final concentration 0.5M), and gently agitated at 4° C. for 3 hours. The sample was added to the suspension containing heparin-sepharose, followed by washing with 10 mM Tris/HCl buffer and loaded into a column. The column was washed with 10 mM Tris/HCl buffer containing 0.7M NaCl (pH 7.4), then the recombinant FGF-5 protein of interest was eluted using 10 mM Tris/HCl buffer and 2 M NaCl solution (pH 7.4) as an eluent. From 4 L *E. coli* culture, 300 μg of partially purified FGF-5 specimen was obtained. The purified specimen was separated by SDS-PAGE, determined for its purity, and stored at −80° C. until use.

Example 1

Preparation of FGF-5 Peptide

The following FGF-5 peptides 1–5 were synthesized by a chemical synthesis method by using a peptide synthesizer and purified by high-performance liquid chromatography or the like. The amino acid sequences of the peptides were analyzed with a protein sequencer, and specimens with a final purity of 80% or higher were obtained.

FGF-5 peptide 1: Pro Asp Gly Lys Val Asn Gly Ser His Glu Ala Asn Met Leu Ser Gln Val His Arg (SEQ ID NO:10)

FGF-5 peptide 2: Pro Asp Gly Lys Val Asn Gly Ser (SEQ ID NO:5)

FGF-5 peptide 3: His Glu Ala Asn Met Leu Ser (SEQ ID NO:6)

FGF-5 peptide 4: His Glu Ala Asn Met Leu Ser Gln Val His Arg (SEQ ID NO:8)

FGF-5 peptide 5: Gln Val His Arg (SEQ ID NO:3)

Example 2

Determination of DNA-Synthesis-Promoting and -Inhibiting Activities of FGF-5 Peptides (1) Determination of DNA-Synthesis-Inhibiting Activity Balb/c3T3 cells (1.5×104 cells/500 μl) were plated on a 24-well culture plate and cultured in a DMEM medium for 24 hours in the presence o f 10% FCS. After washing the cells with the medium, a DMEM medium containing 0.3% FCS was added thereto to further culture the cells for 24 hours to synchronize the cells. To the mixture, test solutions [FGF-5(+)] containing heparin (5 μg/ml), one of FGF-5 peptides 1–5 synthesized in Example 1 ($10^{-7}$ to $10^{-3}$ M) and the recombinant FGF-5 prepared in Reference Example 1 ($10^{-10}$ M) were added. After 16 hours of cultivation, 3 HTdR was added, and the cells were further cultured for 4 hours in a $CO_2$ incubator. The supernatants were aspirated. The cells were washed with PBS, added with 10% TCA (125 μl), and incubated at room temperature. After confirming the immobilization of the cells, the supernatants were discarded. Five-hundred ul of 0.5N NaOH was added and the mixture was further incubated at room temperature for an hour, added with 3 ml scintillator and determined for the uptake of tritium into the cells with a liquid scintillation counter.

(2) Determination of DNA-Synthesis-promoting Activity

The uptake of tritium into cells was determined as described in (1) above with a liquid scintillation counter except that test solutions [FGF-5(−)] containing heparin and one of FGF-5 peptides 1–5 synthesized in Example 1 were used.

As controls for the determinations of inhibiting and promoting activities, a test solution containing heparin (5 μg/ml) and the recombinant FGF-5 ($10^{-10}$ M) prepared in Reference Example 1 was used.

(3) Results

FIGS. 1 to 4 show the results of the determinations of DNA-synthesis-promoting and -inhibiting activities of FGF-5 peptides 1, 3, 4 and 5, respectively.

Figure 1A:
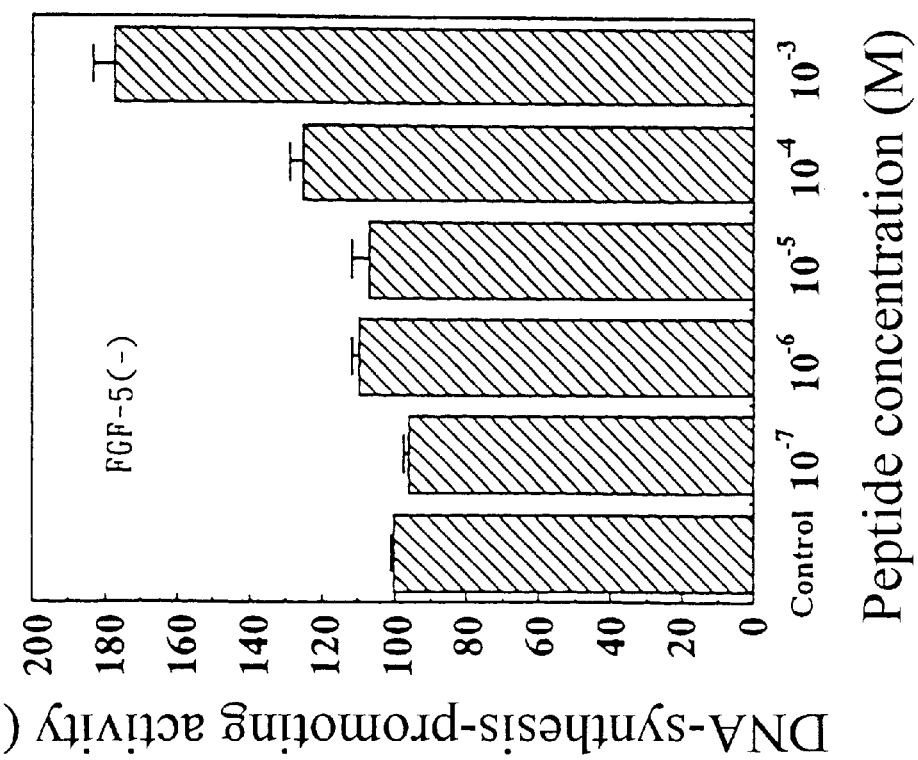

As shown in FIGS. 1 and 2, both FGF-5 peptides 1 and 3 promoted DNA synthesis without the addition of FGF-5.

Figure 4B:
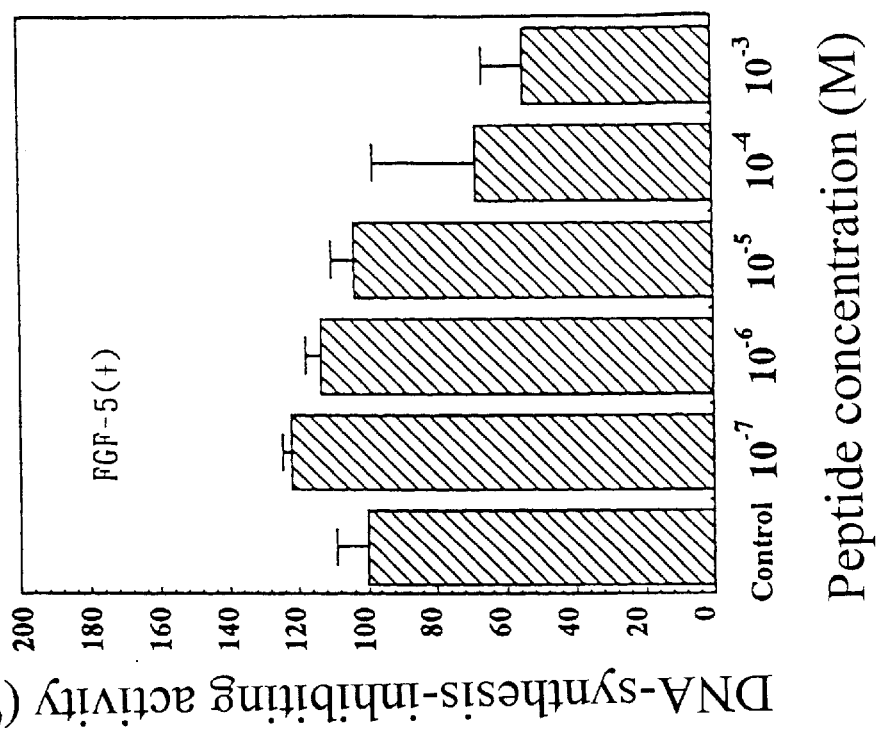
FIGS. 4A and 4B are bar charts showing the results of DNA-synthesis-promoting activity, and DNA-synthesis-inhibiting activity of FGF-5 peptide 5, respectively.
Figure 4A:
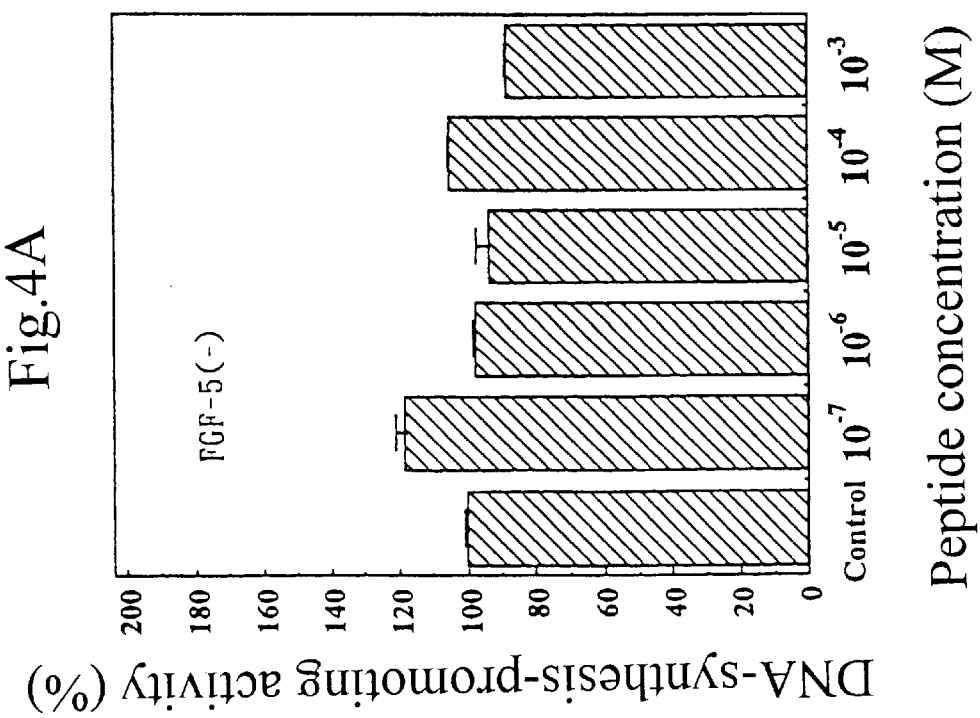

As shown in FIGS. 3 and 4, both FGF-5 peptides 4 and 5 inhibited DNA synthesis promoted by FGF-5.

Example 3 Determination of Differentiating and Proliferating Activities to Give Megakaryocytes by Using Mouse Bone Marrow Cell The following FGF-5 peptide 6 was synthesized in the same manner as described in Example 1.

FGF-5 peptide 6: Pro Asp Gly Lys Val Asn Gly Ser His Glu Ala Asn Met (SEQ ID NO:9).

The differentiating and proliferating activities to give megakaryocytes were determined for this peptide, as the increase of acetylcholineesterase activity, by using mouse bone marrow cells as follows.

Bone marrow cells were taken from femur of ICR mouse (male, 6 weeks old), suspended in RPMI 1640 medium containing 1% fetal calf serum (FCS), and centrifuged. The supernatant was removed and the resultant was suspended in RPMI 1640 medium containing 0.5 mM DFP (diisopropylfluorophosphate) and 0.1% BSA (bovine serum albumin), and left to stand at room temperature for 20 min. Thereafter, the cells were washed with the same culture twice and suspended in RPMI 1640 medium containing 1% Neutridoma-SP and 0.1% BSA such that the number of cells was $2 \times 10^6$ cells/ml. The thus-prepared bone marrow cell suspension was dispensed in 100 µl into a 96-well culture plate, and cultured with a test solution containing 50 µl of FGF-5 peptide 6 at 37° C. for 4 days in the presence of 5% $CO_2$.

Thereafter, the supernatant was removed, and the resultant was washed with PBS(−) twice and added with 180 µl 50 mM HEPES buffer (pH 7.6) containing 0.2% (w/v) Triton X-100 and 0.12 M NaCl and with 20 ul solution containing 5.6 mM acetylthiocholine iodide. After leaving the culture at room temperature for 1 hour, 20 µl of the test solution was taken from each well and transferred to another well, to which 20 µl acetonitrile solution of 0.6 mM 7-diethylamino-3-(4'-maleimidylphenyl)-4-methylcoumarin and 160 µl solution (pH 5.0) containing 0.2% Triton X-100, 1 mM EDTA and 50 mM sodium acetate were added, and left to stand at room temperature for 1 hour. The resultant was subjected to fluorescent measurement (excited at 360 nm and emitted at 460 nm). The results are shown in FIG. 5, which shows that the peptide exerts differentiating and proliferating activities to give megakaryocytes.

Example 4

Determination of Thrombocytosis Activity

ICR mice (male, 6 weeks old, weights 29–32 g) were grouped into 4 groups of six mice. A test solution containing the above-mentioned FGF-5 peptide 6 was intraperitoneally administered for 10 successive days.

The peptide (3.3 mg/ml) in an injection solution (0.9% saline containing 100 µg/ml bovine serum albumin (Fraction V)) was administered to the mice at 0.3 ml/mouse (33 mg/kg) At the same time, human recombinant thrombopoietin solution (0.1 µg/ml) and human recombinant interleukin 6 solution (0.1 µg/ml) were prepared, and intraperitoneally administered for 0.3 ml per mouse (1 µg/kg). Five µl of blood was collected from the caudal vein of each mouse, and immediately mixed with 20 µl of 3.8% sodium citrate in a test tube. Subsequently, the blood mixtures were serially diluted twice with Cellpack and determined for the number of platelets, as well as to determine the numbers of erythrocytes and hemacrit values with Sysmex F-820 (TOA Electronics Ltd.)

Two to 4 days after the administration, the numbers of platelets in the mice administered with the peptide increased 1.6 folds, showing the platelet increasing activity of the peptide. Similarly, about 1.6 fold-increase of platelet was observed for the mice groups administered with human recombinant thrombopoietin and human recombinant interleukin 6. No mouse in any of the administration group died nor had reduced weight during the experiment.

Accordingly, the above-described peptide is expected for its use as a platelet regulating substance that can be used without causing a harmful effect.

According to the present invention, a peptide is provided which can control various physiological functions of FGF-5. A pharmaceutical composition containing the peptide of the invention as an active component is able to regulate the physiological functions of FGF-5, for example, to regulate development or growth of a head or body hair, to regulate nutrition or function of a cranial nerve system, to regulate platelets, and to proliferate fibroblasts or vascular endothelial cells.

All publications, patents and patent applications cited herein are incorporated herein by reference in their entirety.

What is claimed is:

1. An isolated peptide consisting of an amino acid sequence of SEQ ID NO:9.

2. An isolated peptide consisting of an amino acid sequence as set forth in SEQ ID NO:3.

3. An isolated peptide consisting of an amino acid sequence as set forth in SEQ ID NO:6.

4. An isolated peptide consisting of an amino acid sequence as set forth in SEQ ID NO:8.

5. An isolated peptide consisting of an amino acid sequence as set forth in SEQ ID NO:10.

* * * * *

SEQUENCE LISTING

```
<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: SEQ ID NO:1 represents a partial sequence
      (corresponding to amino acids 105-119) of the amino acid
      sequence of human FGF-5.

<400> SEQUENCE: 1

Pro Asp Gly Lys Val Asn Gly Ser His Glu Ala Asn Met Leu Ser
```

-continued

```
1               5               10              15

<210> SEQ ID NO 2
<211> LENGTH: 15
<212> TYPE: PRT
<213> ORGANISM: Artificial Sequence
<220> FEATURE:
<223> OTHER INFORMATION: SEQ ID NO:2 represents a partial sequence
      (corresponding to amino acids 103-117) of the amino acid
      sequence of mouse FGF-5.

<400> SEQUENCE: 2

Pro Asp Gly Lys Val Asn Gly Ser His Glu Ala Ser Val Leu Ser
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: SEQ ID NO:3 represents a partial sequence
      (corresponding to amino acids 120-123) of the amino acid
      sequence of human FGF-5S.

<400> SEQUENCE: 3

Gln Val His Arg
1

<210> SEQ ID NO 4
<211> LENGTH: 4
<212> TYPE: PRT
<213> ORGANISM: Artificial Sequence
<220> FEATURE:
<223> OTHER INFORMATION: SEQ ID NO:4 represents a partial sequence
      (corresponding to amino acids 118-121) of the amino acid
      sequence of mouse FGF-5S.

<400> SEQUENCE: 4

Gln Ile Tyr Gly
1

<210> SEQ ID NO 5
<211> LENGTH: 8
<212> TYPE: PRT
<213> ORGANISM: Artificial Sequence
<220> FEATURE:
<223> OTHER INFORMATION: SEQ ID NO:5 represents a partial sequence
      (corresponding to amino acids 105-112) of the amino acid
      sequence of human FGF-5, or a partial sequence (corresponding
      to amino acids 103-110) of the amino acid sequence of mouse FGF-5.

<400> SEQUENCE: 5

Pro Asp Gly Lys Val Asn Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: SEQ ID NO:6 represents a partial sequence
      (corresponding to amino acids 113-119) of the amino acid
      sequence of human FGF-5.

<400> SEQUENCE: 6

His Glu Ala Asn Met Leu Ser
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: SEQ ID NO:7 represents a partial sequence
      (corresponding to amino acids 111-117) of the amino acid
      sequence of mouse FGF-5.

<400> SEQUENCE: 7

His Glu Ala Ser Val Leu Ser
 1               5

<210> SEQ ID NO 8
<211> LENGTH: 11
<212> TYPE: PRT
<213> ORGANISM: Artificial Sequence
<220> FEATURE:
<223> OTHER INFORMATION: SEQ ID NO:8 represents a partial sequence
      (corresponding to amino acids 113-123) of the amino acid
      sequence of human FGF-5S.

<400> SEQUENCE: 8

His Glu Ala Asn Met Leu Ser Gln Val His Arg
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: SEQ ID NO:9 represents a partial sequence
      (corresponding to amino acids 105-117) of the amino acid
      sequence of human FGF-5.

<400> SEQUENCE: 9

Pro Asp Gly Lys Val Asn Gly Ser His Glu Ala Asn Met
 1               5                  10

<210> SEQ ID NO 10
<211> LENGTH: 19
<212> TYPE: PRT
<213> ORGANISM: Artificial Sequence
<220> FEATURE:
<223> OTHER INFORMATION: SEQ ID NO:10 represents a partial sequence of
      the amino acid sequence of human FGF-5.

<400> SEQUENCE: 10

Pro Asp Gly Lys Val Asn Gly Ser His Glu Ala Asn Met Leu Ser Gln
 1               5                  10                  15

Val His Arg
```